(12) United States Patent
Failli et al.

(10) Patent No.: US 7,329,653 B2
(45) Date of Patent: Feb. 12, 2008

(54) CYCLOHEXYLPHENYL VASOPRESSIN AGONISTS

(75) Inventors: Amedeo A. Failli, Princeton Junction, NJ (US); Jay S. Shumsky, Hightstown, NJ (US); Thomas J. Caggiano, Morrisville, PA (US); John P. Dusza, Nanuet, NY (US); Kevin A. Memoli, Cranbury, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/403,072

(22) Filed: Apr. 11, 2006

(65) Prior Publication Data

US 2006/0183734 A1 Aug. 17, 2006

Related U.S. Application Data

(62) Division of application No. 10/120,917, filed on Apr. 11, 2002, now Pat. No. 7,053,083.

(60) Provisional application No. 60/283,387, filed on Apr. 12, 2001.

(51) Int. Cl.
*A61P 13/00* (2006.01)
*A61K 31/55* (2006.01)
*C07D 487/00* (2006.01)

(52) U.S. Cl. .................. 514/215; 514/217; 514/220; 540/554; 540/559; 540/561; 540/577; 540/578; 540/587

(58) Field of Classification Search ............... 514/215, 514/217, 220; 540/554, 559, 561, 577, 578, 540/587
See application file for complete search history.

(56) References Cited

U.S. PATENT DOCUMENTS

| 5,516,774 | A | 5/1996 | Albright et al. | 514/220 |
| 5,521,173 | A | 5/1996 | Venkatesan et al. | 514/220 |
| 5,532,235 | A | 7/1996 | Albright et al. | 514/215 |
| 5,536,718 | A | 7/1996 | Albright et al. | 514/220 |
| 5,610,156 | A | 3/1997 | Albright et al. | 514/220 |
| 5,612,334 | A | 3/1997 | Albright et al. | 514/220 |
| 5,624,923 | A | 4/1997 | Albright et al. | 514/220 |
| 5,654,297 | A | 8/1997 | Albright et al. | 514/215 |
| 5,686,445 | A | 11/1997 | Albright et al. | 514/211 |
| 5,693,635 | A | 12/1997 | Albright et al. | 514/215 |
| 5,696,112 | A | 12/1997 | Albright et al. | 514/215 |
| 5,700,796 | A | 12/1997 | Albright et al. | 514/220 |

(Continued)

FOREIGN PATENT DOCUMENTS

| WO | WO 9534540 | 12/1995 |
| WO | WO 9622282 | 7/1996 |
| WO | WO 9722591 | 6/1997 |
| WO | WO 9965525 | 12/1999 |
| WO | WO 0043398 | 7/2000 |

(Continued)

OTHER PUBLICATIONS

Kondo et al., Novel Design of Nonpeptide A VP V2 Receptor Agonists: Structural Requirements for an Agonist Having 1-(4-Aminobenzoyl)-2,3,4,5-tetrahydro-1H-1-benzazepine as a Template, J. of Medicinal Chemistry, Nov. 2000, vol. 43, No. 23, pp. 4388-4397.

(Continued)

*Primary Examiner*—Brenda Coleman
(74) *Attorney, Agent, or Firm*—Pepper Hamilton LLP

(57) ABSTRACT

The present invention provides compounds of the general formulas:

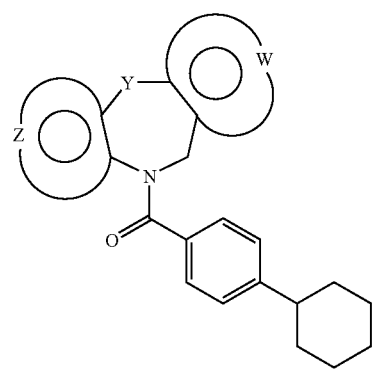

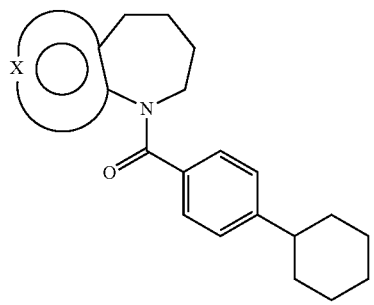

wherein Y is NR or —(CH$_2$)$_n$; R is H or alkyl; "Z" represents optionally substituted phenyl or a 6-membered aromatic ring having one nitrogen atom; "W" represents a optionally substituted phenyl or 5-membered aromatic ring having one nitrogen atom; "X" represents an optionally substituted 5-membered aromatic ring having one sulfur atom; as well as methods and pharmaceutical compositions utilizing these compounds for the inducing temporary delay of urination or treatment of disorders remedied by vasopressin agonist activity, including diabetes insipidus, nocturnal enuresis, nocturia, urinary incontinence, or bleeding and coagulation disorders.

8 Claims, No Drawings

U.S. PATENT DOCUMENTS

| | | |
|---|---|---|
| 5,719,278 A | 2/1998 | Albright et al. ............ 540/578 |
| 5,733,905 A | 3/1998 | Albright et al. ............ 514/220 |
| 5,736,538 A | 4/1998 | Albright et al. ............ 514/215 |
| 5,736,540 A | 4/1998 | Albright et al. ............ 514/220 |
| 5,739,128 A | 4/1998 | Albright et al. ............ 514/220 |
| 5,747,487 A | 5/1998 | Albright et al. ............ 514/215 |
| 5,753,648 A | 5/1998 | Albright et al. ............ 514/220 |
| 5,760,031 A | 6/1998 | Albright et al. ............ 514/215 |
| 5,780,471 A | 7/1998 | Venkatesan et al. ........ 514/250 |
| 5,849,735 A | 12/1998 | Albright et al. ............ 514/220 |
| 6,096,735 A | 8/2000 | Ogawa et al. ......... 514/213.01 |
| 6,096,736 A | 8/2000 | Ogawa et al. ......... 514/213.01 |

OTHER PUBLICATIONS

Erstad, Systemic Hemostatic Medications for Reducing Surgical Blood Loss, The Annals of Pharmacotherapy, Jul./Aug. 2001, vol. 35, pp. 925-934.

Wong et al., Desmopressin Does Not Decrease Blood Loss and Transfusion Requirements in Patients Undergoing Hepatectomy, 2003, vol. 50, No. 1, pp. 14-20.

Beitz and Schultz, Current Medicinal Chemistry, 1999, 457-467, 6. cited by other. Goodman and Gilman, The Pharmacological Basis of Therapeutics, 1996, 715-731, 9th Edition.

Lethagen, Ann. Hematol., 1994, 173-180, 69.27.

Cash et al., Brit. J. Haematol., 1974, 363-364.

David, Regulatory Peptides, 1993, 311-317, 45.

Burggraaf et al., Cli. Sci., 1994, 497-503, 86.

CYCLOHEXYLPHENYL VASOPRESSIN AGONISTS

CROSS-REFERENCE TO RELATED APPLICATIONS

This application is a divisional application of application Ser. No. 10/120,917, Filed: Apr. 11, 2002, which claims priority under 35 U.S.C. § 119(e) to Provisional Application Ser. No. 60/283,387, Filed: Apr. 12, 2001, all applications incorporated herein by reference in their entireties.

This invention concerns cyclohexylphenyls which act as vasopressin $V_2$ agonists, as well as methods of treatment and pharmaceutical compositions utilizing these compounds.

BACKGROUND OF THE INVENTION

Vasopressin plays a vital role in the conservation of water by concentrating the urine in the collecting ducts of the kidney. The collecting ducts of the kidney are relatively impermeable to water without the presence of vasopressin at the receptors and therefore, the hypotonic fluid formed after filtering through the glomeruli, passing the proximal convoluted tubule, the loops of Henle, and the distal convoluted tubules, will be excreted as dilute urine. However, during dehydration, volume depletion or blood loss, vasopressin is released from the brain and activates the vasopressin $V_2$ receptors in the collecting ducts of the kidney rendering the ducts very permeable to water; hence water is reabsorbed and a concentrated urine is excreted. Aquaporins (water channel membrane proteins) play a major role in this intricate process (for a review on mammalian aquaporins, see Beitz and Schultz, *Current Medicinal Chemistry*, 6, 457-467 (1999)). In patients and animals with central or neurogenic diabetes insipidus, the synthesis of vasopressin in the brain is defective and therefore, they produce very little or no vasopressin, but their vasopressin receptors in the kidneys are normal. Because they cannot concentrate the urine, they may produce as much as 10 times the urine volumes of their healthy counterparts and are very sensitive to the action of vasopressin and vasopressin $V_2$ agonists. Vasopressin and desmopressin, (1-desamino-8D-arginine vasopressin) which is a peptide analog of the natural vasopressin, are being used in patients with central diabetes insipidus. Vasopressin $V_2$ agonists are also useful for the treatment of nocturnal enuresis, nocturia, urinary incontinence and temporary delay of urination, whenever desirable.

Vasopressin, through activation of its $V_{1a}$ receptors, exerts vasoconstricting effects so as to raise blood pressure. A vasopressin $V_{1a}$ receptor antagonist will counteract this effect. Vasopressin and vasopressin-like agonists cause release factor VIII and von Willebrand factor from intracellular stores, so they are useful for the treatment of bleeding disorders, such as hemophilia. Vasopressin and vasopressin-like agonists also release tissue-type plasminogen activator (t-PA) into the blood circulation so they are useful in dissolving blood clots such as in patients with myocardial infarction and other thromboembolic disorders (Jackson, "Vasopressin and other agents affecting the renal conservation of water", in Goodman and Gilman, *The Pharmacological Basis of Therapeutics*, 9th ed., Hadman, Limbird, Molinoff, Ruddon and Gilman Eds., McGraw-Hill, New York, pp. 715-731 (1996); Lethagen, *Ann. Hematol.* 69, 173-180 (1994); Cash et al., *Brit. J. Haematol.*, 27, 363-364 (1974); David, *Regulatory Peptides*, 45, 311-317 (1993); Burggraaf et al., *Cli. Sci.*, 86, 497-503 (1994)).

Non-peptidic vasopressin antagonists have recently been disclosed. Albright et al. describe tricyclic azepines as vasopressin antagonists or vasopressin and oxytocin antagonists in U.S. Pat. No. 5,516,774 (1996), U.S. Pat. No. 5,532,235 (1996), U.S. Pat. No. 5,536,718 (1996), U.S. Pat. No. 5,610,156 (1997), U.S. Pat. No. 5,612,334 (1997), U.S. Pat. No. 5,624,923 (1997), U.S. Pat. No. 5,654,297 (1997), U.S. Pat. No. 5,686,445 (1997), U.S. Pat. No. 5,693,635 (1997), U.S. Pat. No. 5,696,112 (1997), U.S. Pat. No. 5,700,796 (1997), U.S. Pat. No. 5,719,278 (1998), U.S. Pat. No. 5,733,905 (1998), U.S. Pat. No. 5,736,538 (1998), U.S. Pat. No. 5,736,540 (1998), U.S. Pat. No. 5,739,128 (1998), U.S. Pat. No. 5,747,487 (1998), U.S. Pat. No. 5,753,648 (1998), U.S. Pat. No. 5,760,031 (1998), U.S. Pat. No. 5,780,471 (1998); tetrahydrobenzodiazepine derivatives as vasopressin antagonists are disclosed in J.P. 0801460-A (1996); Ogawa et al., disclose benzoheterocyclic derivatives as vasopressin and oxytocin antagonists, and as vasopressin agonists in WO 9534540-A; Ogawa et al. disclose benzazepine derivatives with anti-vasopressin activity, oxytocin antagonistic activity and vasopressin agonist activity, useful as vasopressin antagonists, vasopressin agonists and oxytocin antagonists in WO 97/22591 (1997) and U.S. Pat. No. 6,096,736 (2000); and Venkatesan et al., disclose tricyclic benzazepine derivatives as vasopressin and oxytocin antagonists in U.S. Pat. No. 5,521,173 (1996). Ohtake et al. disclose ocular tension lowering agents and phosphoric ester derivatives exhibiting vasopressin $V_1$ receptor antagonism in WO 99/65525 (1999); and Hoekstra et al. disclose tricyclic benzodiazepines useful as vasopressin receptor antagonists for treating conditions involving increased vascular resistance and cardiac insufficiency in WO 00/43398 (2000).

Albright et al., disclose without apparent exemplification, a subset of tricyclic dibenzodiazepines, pyrrolo benzodiazepines and pyrrolo pyridodiazepines part of the present application, as $V_1$ and/or $V_2$ vasopressin receptor antagonists and oxytocin receptor antagonists in U.S. Pat. No. 5,849,735 (1998) and WO 96/22282 A1 (1996), inter alia.

Albright et al., also disclose a subset of tricyclic pyrrolo pyridodiazepines as $V_1$ and/or $V_2$ vasopressin receptor antagonists and oxytocin receptor antagonists in U.S. Pat. No. 5,532,235 (1996).

Albright et al., also teach a subset of tricyclic pyrrolo benzodiazepines and pyrrolo pyridodiazepines as $V_1$ and/or $V_2$ vasopressin receptor antagonists and oxytocin receptor antagonists in U.S. Pat. No. 5,624,923 (1997) and U.S. Pat. No. 5,736,540 (1998).

Albright et al., also describe a subset of thienoazepines as $V_1$ and/or $V_2$ vasopressin receptor antagonists and oxytocin receptor antagonists in U.S. Pat. No. 5,654,297 (1997) and U.S. Pat. No. 5,696,112 (1997).

SUMMARY OF THE INVENTION

This invention relates to novel and known compounds selected from those of formula (I) or (II):

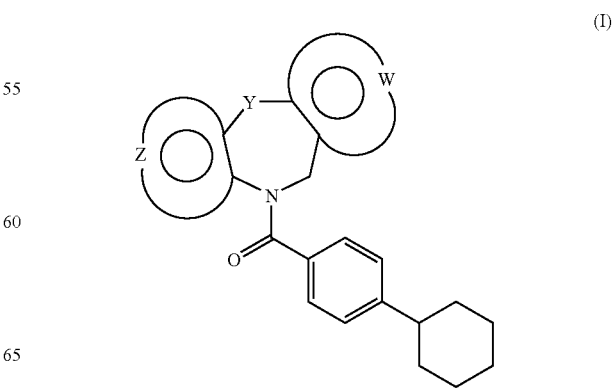

-continued (II)

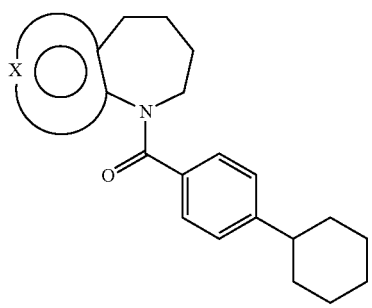

wherein:

Y is a moiety selected from NR or —(CH$_2$)$_n$;

wherein R is hydrogen or (C$_1$-C$_6$) lower alkyl, and n is 1;

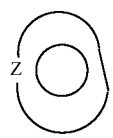

represents (1) a phenyl ring optionally substituted with one or two substituents selected, independently, from the group comprising hydrogen, (C$_1$-C$_6$) lower alkyl, halogen, cyano, CF$_3$, —OCF$_3$, hydroxy, (C$_1$-C$_6$) lower alkoxy, or (C$_1$-C$_6$) lower alkoxy carbonyl; carboxy, —CONH$_2$, —CONH[(C$_1$-C$_6$) lower alkyl], —CON[(C$_1$-C$_6$) lower alkyl]$_2$; or (2) a 6-membered aromatic (unsaturated) heterocyclic ring having one nitrogen atom, optionally substituted by (C$_1$-C$_6$) lower alkyl, halogen or (C$_1$-C$_6$) lower alkoxy;

represents (1) a a phenyl ring optionally substituted with one or two substituents selected, independently, from the group comprising hydrogen, (C$_1$-C$_6$) lower alkyl, halogen, cyano, CF$_3$, hydroxy, (C$_1$-C$_6$) lower alkoxy, or (C$_1$-C$_6$) lower alkoxy carbonyl; carboxy, —CONH$_2$, —CONH[(C$_1$-C$_6$) lower alkyl], —CON[(C$_1$-C$_6$) lower alkyl]$_2$; or (2) a 5-membered aromatic (unsaturated) heterocyclic ring having one nitrogen atom, optionally substituted by (C$_1$-C$_6$) lower alkyl, (C$_1$-C$_6$) lower alkoxy, or halogen; or (3) a 6-membered aromatic (unsaturated) heterocyclic ring having one nitrogen atom, optionally substituted by (C$_1$-C$_6$) lower alkyl, halogen, or (C$_1$-C$_6$) lower alkoxy;

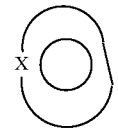

represents a 5-membered aromatic (unsaturated) heterocyclic ring having one sulfur atom, optionally substituted by (C$_1$-C$_6$) lower alkyl, halogen, or (C$_1$-C$_6$) lower alkoxy;

or a pharmaceutically acceptable salt, or pro-drug form thereof.

One group of compounds of this invention comprise those of the formula:

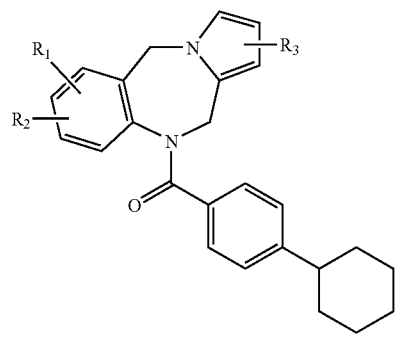

wherein:

R$_1$ and R$_2$ are independently selected from H, C$_1$-C$_6$ alkyl, halogen, CN, CF$_3$, —OCF$_3$, OH, C$_1$-C$_6$ alkoxy, or C$_1$-C$_6$ alkoxy carbonyl; carboxy, —CONH$_2$, —CONH[C$_1$-C$_6$ alkyl], —CON[C$_1$-C$_6$ alkyl]$_2$; and R$_3$ is selected from the group of C$_1$-C$_6$ alkyl, C$_1$-C$_6$ alkoxy, or halogen;

or a pharmaceutically acceptable salt thereof.

Another group of this invention comprises the compounds of the formula:

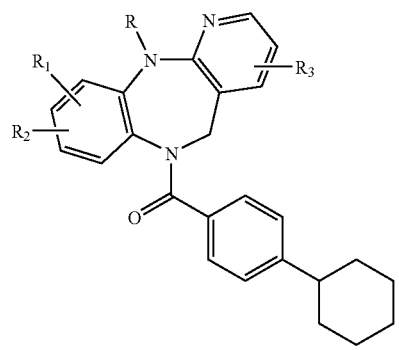

wherein:

R is H or C$_1$-C$_6$ alkyl;

$R_1$ and $R_2$ are independently selected from H, $C_1$-$C_6$ alkyl, halogen, CN, $CF_3$, —$OCF_3$, OH, $C_1$-$C_6$ alkoxy, or $C_1$-$C_6$ alkoxy carbonyl; carboxy, —$CONH_2$, —$CONH[C_1$-$C_6$ alkyl], —$CON[C_1$-$C_6$ alkyl]$_2$; and $R_3$ is selected from the group of $C_1$-$C_6$ alkyl, $C_1$-$C_6$ alkoxy, or halogen;

or a pharmaceutically acceptable salt thereof.

A further group of compounds of this invention comprise those of the formula:

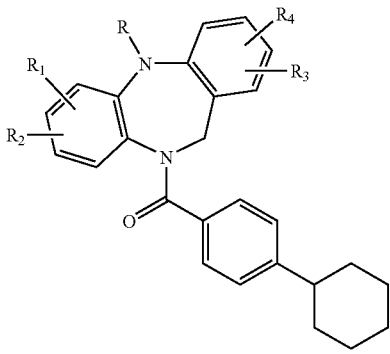

wherein:

R is H or $C_1$-$C_6$ alkyl; and $R_1$, $R_2$, $R_3$ and $R_4$ are each independently selected from H, $C_1$-$C_6$ alkyl, halogen, CN, $CF_3$, —O—$CF_3$, OH, $C_1$-$C_6$ alkoxy, or $C_1$-$C_6$ alkoxy carbonyl; carboxy, —$CONH_2$, —$CONH[C_1$-$C_6$ alkyl], —$CON[C_1$-$C_6$ alkyl]$_2$;

or a pharmaceutically acceptable salt thereof.

Another group of compounds of this invention comprises those of the formula:

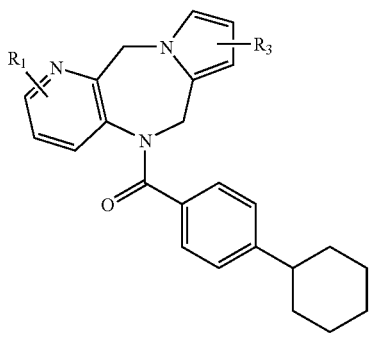

wherein:

$R_1$ is selected from $C_1$-$C_6$ alkyl, halogen or $C_1$-$C_6$ alkoxy; and $R_3$ is selected from the group of $C_1$-$C_6$ alkyl, $C_1$-$C_6$ alkoxy, or halogen;

or a pharmaceutically acceptable salt thereof.

As used herein the term "lower", as used in relation to alkoxy or alkyl, is understood to refer to those groups having from 1 to 6 carbon atoms. Halogen refers to fluorine, chlorine, bromine or iodine.

The preferred compounds of this invention are:
1. 10-(4-Cyclohexyl-benzoyl)-10,11-dihydro-5H-pyrrolo[2,1-c][1,4]benzodiazepine;
2. (4-Cyclohexyl-phenyl)-(5,11-dihydro-pyrido[2,3-b][1,5]benzodiazepin-6-yl)-methanone;
3. (4-Cyclohexyl-phenyl)-(5,11-dihydro-11-methyl-5H-pyrido[2,3-b][1,5]benzodiazepin-6-yl)-methanone;
4. (4-Cyclohexyl-phenyl)-(5,11-dihydro-11-ethyl-5H-pyrido[2,3-b][1,5]benzodiazepin-6-yl)-methanone;
5. (4-Cyclohexyl-phenyl)-(5,11-dihydro-10H-dibenzo[b,e][1,4]diazepin-10-yl)-methanone;
6. (4-Cyclohexyl-phenyl-(5,11-dihydro-5-methyl-10H-dibenzo[b,e][1,4]diazepin-10-yl)-methanone;
7. (4-Cyclohexyl-phenyl)-(4H,10H-3a,5,9-triaza-benzo[f]azulen-9-yl)-methanone;
8. (4-Cyclohexyl-phenyl)-(5,6,7,8-tetrahydro-thieno[3,2-b]azepin-4-yl)-methanone;

It is understood by those practicing the art that some of the compounds of this invention may contain one or more asymmetric centers and may thus give rise to optical isomers and diastereomers. The present invention includes such optical isomers and diastereomers; as well as the racemic and resolved, enantiomerically pure R and S stereoisomers and pharmaceutically acceptable salts thereof, which possess the indicated activity. Optical isomers may be obtained in pure form by standard procedures known to those skilled in the art. It is also understood that this invention encompasses all possible regioisomers, and mixtures thereof which possess the indicated activity. Such regioisomers may be obtained in pure form by standard separation procedures known to those skilled in the art.

Also according to the present invention there is provided a method of treating disorders which are remedied or alleviated by vasopressin receptor agonist activity including, but not limited to, diabetes insipidus, nocturnal enuresis, nocturia, urinary incontinence, bleeding and coagulation disorders, and temporary delay of urination whenever desirable in humans or other mammals, which comprises administering to a human or other mammal an effective amount of a compound or a pharmaceutical composition of the invention.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may be adapted for other modes of administration, for example, parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 1000 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day. The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

Also according to the present invention there are provided processes for producing the compounds of the present invention.

PROCESS OF THE INVENTION

The compounds of the present invention of general formula (I) may conveniently be prepared according to the process shown in Scheme 1.

Scheme 1

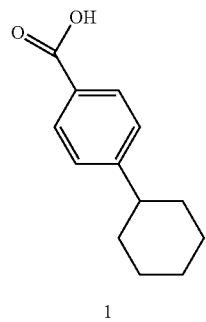

1

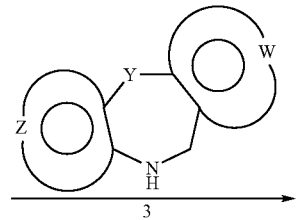

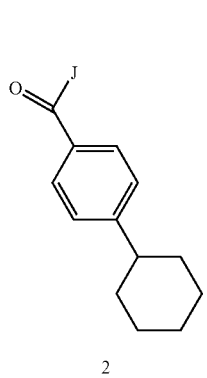

2

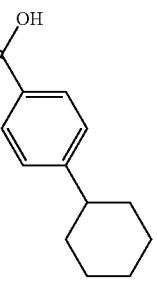

(I)

Thus, a tricyclic diazepine of formula (3) is treated with an appropriately activated cyclohexyl carboxylic acid derivative of formula (2) to provide the desired compounds of formula (I) wherein Y is a moiety selected from NR or —$(CH_2)_n$; wherein R is hydrogen or ($C_1$-$C_6$) lower alkyl and n is 1; and

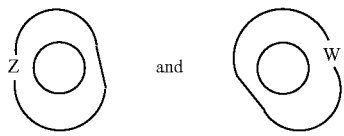

are as defined hereinbefore.

Likewise, treatment of an appropriately activated cyclohexyl carboxylic acid derivative of formula (2) with a bicyclic azepine of formula (4) as shown in Scheme 2 provides the desired compounds of formula (II), wherein

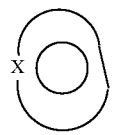

is as defined hereinbefore.

Scheme 2

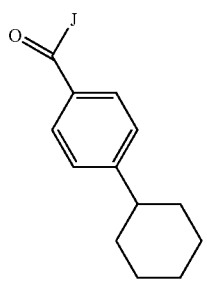

1

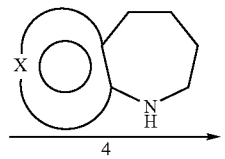

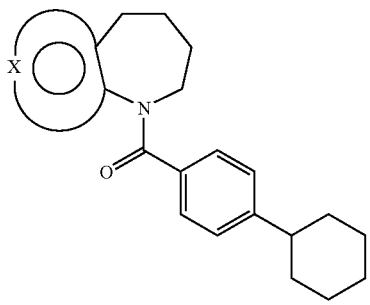

(II)

The cyclohexyl carboxylic acid of formula (1) may be activated as the acid halide, preferably the acid chloride (J=Cl), and reacted with the tricyclic diazepine of formula (3) or the bicyclic azepine of formula (4) respectively, in the presence of an inorganic base such as potassium carbonate in a polar, aprotic solvent such as N,N-dimethylformamide; or an organic base such as N,N-diisopropylethyl amine or 4-(dimethylamino)pyridine in an aprotic solvent, such as dichloromethane or tetrahydrofuran, at temperatures ranging from −20° C. to 50° C.

Alternatively, the acylating species of formula (2) can be a mixed anhydride of the aforementioned carboxylic acid, such as that prepared by treating said acid with 2,4,6-trichlorobenzoyl chloride in an aprotic organic solvent such as dichloromethane, according to the procedure of Inanaga et al., *Bull. Chem. Soc. Jpn.*, 52, 1989 (1979). Treatment of the mixed anhydride of formula (2) with the tricyclic diazepine of formula (3) or the bicyclic azepine of formula (4) in an aprotic solvent such as dichloromethane, and in the presence of an organic base such as 4-(dimethylamino) pyridine at temperatures ranging from 0° C. to the reflux temperature of the solvent, yields a compound of formula (I) or (II) respectively, wherein Y,

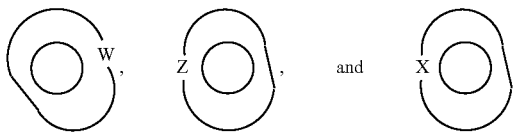

are as defined above.

Alternatively, the activation of the carboxylic acid of formula (1) can be carried out by reacting said acid with other peptide coupling reagents known to those skilled in the art, in an organic aprotic solvent such as dichloromethane, tetrahydrofuran, N,N-dimethylformamide, and the like, at temperatures ranging from 0° C. to 120° C.

The activating agent for the carboxylic acid of formula (1) is ultimately chosen on the basis of its reactivity with the tricyclic diazepine of formula (3) or the bicyclic azepine of formula (4), respectively.

The subject compounds of the present invention were tested for biological activity according to the following procedures.

Vasopressin $V_2$ Agonist Effects of Test Compounds in Normal Conscious Water-Loaded Rats Male or female normotensive Sprague-Dawley rats (Charles River Laboratories, Inc., Kingston, N.Y.) of 350-500 g body weight were supplied with standard rodent diet (Purina Rodent Lab. Chow 5001) and water ad libitum. On the day of test, rats were placed individually into metabolic cages equipped with devices to separate the feces from the urine and containers for collection of urine. A test compound or a reference agent was given at an oral dose of 10 mg/Kg in a volume of 10 mL/Kg. The vehicle used was 2.5% preboiled corn starch in 20% dimethylsulfoxide (DMSO). Thirty minutes after dosing the test compound, rats were gavaged with water at 30 mL/Kg into the stomach using a feeding needle. During the test, rats were not provided with water or food. Urine was collected for four hours after dosing of the test compound. At the end of four hours, urine volume was measured. Urinary osmolality was determined using a Fiske One-Ten Osmometer (Fiske Associates, Norwood, Mass., 02062) or an Advanced CRYOMATIC Osmometer, Model 3C2 (Advanced Instruments, Norwood, Mass.). Determinations of $Na^+$, $K^+$ and $Cl^-$ ion were carried out using ion specific electrodes in a Beckman SYNCHRON EL-ISE Electrolyte System analyzer. The urinary osmolality should increase proportionally. In the screening test, two rats were used for each compound. If the difference in the urine volume of the two rats was greater than 50%, a third rat was used.

The results of this study are shown in Table 1.

TABLE 1

| Example | Urine Volume (% decrease)[a] | Urinary Osmolality (% increase)[b] | Rat Type[c] |
|---------|------------------------------|------------------------------------|-------------|
| 1 | 61 | 232 | CD |
| 2 | 48 | 51 | CD |
| 3 | 51 | 129 | CD |
| 4 | 64 | 132 | CD |

[a]Percent decrease in urine volume vs control at a dose of 10 mg/Kg
[b]Percent increase in osmolality vs control at a dose of 10 mg/Kg
[c]Rat model used: Sprague-Dawley (CD)

The following examples are presented to illustrate rather than limit the scope of the invention.

EXAMPLE 1

10-(4-Cyclohexyl-benzoyl)-10,11-dihydro-5H-pyrrolo[2,1-c][1,4]benzodiazepine

A suspension of 4-cyclohexylbenzoic acid (0.50 g, 2.45 mmol) in thionyl chloride (3 mL) was heated at reflux for 30 minutes. After cooling, the thionyl chloride was removed in vacuo. The residue was dissolved in toluene and concentrated in vacuo to give the crude acid chloride as a yellow oil. The acid chloride was then dissolved in dichloromethane (5 mL) and slowly added to a solution of 10,11-dihydro-5H-pyrrolo[2,1-c][1,4]benzodiazepine (0.67 g, 3.64 mmol) and N,N-diisopropylethyl amine (0.94 mL, 5.4 mmol) in dichloromethane (15 mL). After stirring for 2 hours, the reaction was quenched with water. The layers were separated, and the organic layer was washed with 1 N hydrochloric acid, 1 N sodium hydroxide and brine, dried over anhydrous sodium sulfate, filtered and concentrated in vacuo to give a yellow oil. Purification by flash chromatography using a solvent system of 50% dichloromethane in hexane followed by 25% ethyl acetate in hexane, gave a white foam which crystallized upon sonication from hexane/ethyl acetate to provide the title compound (0.60 g, 66.1%) as a white solid, mp 127-129° C.

NMR (DMSO-$d_6$, 400 MHz): δ 1.15-1.32 (m, 5H), 1.64-1.74 (m, 5H), 2.39-2.42 (m, 1H), 4.80-5.40 (broad s, 4H), 5.91-5.94 (m, 2H), 6.81 (t, 1H), 6.90 (d, 1H), 7.05-7.11 (m, 3H), 7.15-7.19 (m, 3H), 7.45-7.47 (m, 1H).

MS [EI, m/z]: 370 $[M]^+$.

Anal. Calcd. for $C_{25}H_{26}N_2O+0.05C_4H_8O_2$: C 80.74, H 7.10, N 7.47. Found: C 80.36, H 7.11, N 7.53.

EXAMPLE 2

(4-Cyclohexyl-phenyl)-(5,11-dihydro-pyrido[2,3-b][1,5]benzodiazepin-6-yl)-methanone A suspension of 4-cyclohexylbenzoic acid (1.30 g, 6.4 mmol) in thionyl chloride (6 mL) was heated at reflux for 30 minutes. After cooling, the thionyl chloride was removed in vacuo. The residue was dissolved in toluene and concentrated in vacuo to give the acid chloride as a golden oil. The acid chloride was then dissolved in N,N-dimethylformamide (5 mL) and slowly added to a solution of 6,11-dihydro-5H-pyrido[2,3-b][1,5]benzodiazepine (1.0 g, 5.1 mmol) and potassium carbonate (0.77 g, 5.6 mmol) in N,N-dimethylformamide (15 mL). After stirring for one hour, the reaction was quenched with water and extracted with ethyl acetate. The organic extracts were washed with 1 N sodium hydroxide, dried over anhydrous sodium sulfate, filtered and concentrated in vacuo to give a light pink solid. The solid was dissolved in a large volume of boiling ethanol and filtered hot. The title compound (1.19 g) crystallized as an off-white solid, m.p. 230-233° C.

NMR (DMSO-$d_6$, 400 MHz): δ 1.11-1.32 (m, 5H), 1.63-1.71 (m, 5H), 2.30-2.41 (m, 1H), 4.05 (d, 1H), 5.55 (d, 1H), 6.52-6.61 (m, 2H), 6.71-6.74 (m, 1H), 7.01-7.06 (m, 5H), 7.28-7.31 (m, 1H), 7.51-7.52 (m, 1H), 8.07-8.08 (m, 1H), 9.55 (s, 1H).

MS [(+)ESI, m/z]: 384 [M+H]$^+$.

Anal. Calcd. for $C_{25}H_{25}N_3O+0.08C_2H_6O$: C 78.05, H 6.63, N 10.85. Found: C 77.76, H 6.65, N 10.79.

EXAMPLE 3

(4-Cyclohexyl-phenyl)-(5,11-dihydro-11-methyl-5H-pyrido[2,3-b][1,5]benzodiazepin-6-yl)-methanone Sodium hydride (60% suspension in oil, 0.070 g, 1.75 mmol) was washed twice with hexane, dried under nitrogen and resuspended in dry N,N-dimethylformamide (10 mL). Following addition of (4-cyclohexyl-phenyl)-(5,11-dihydro-pyrido[2,3-b][1,5]benzodiazepin-6-yl)-methanone of Example 2 (0.50 g, 1.30 mmol), methyl iodide (0.10 mL, 1.60 mmol) was added. After stirring for one hour, the reaction was quenched with water and extracted with dichloromethane The organic extracts were dried over anhydrous sodium sulfate, filtered and concentrated in vacuo to give a yellow solid. Purification by flash chromatography using a solvent system of 30% ethyl acetate in hexane provided the title compound (0.17 g, 32.9%) as a white solid, m.p. 136-138° C.

NMR (DMSO-$d_6$, 400 MHz): δ 1.13-1.34 (m, 5H), 1.63-1.74 (m, 5H), 2.37-2.42 (m, 1H), 3.51 (s, 3H), 4.28 (broad s, 1H), 5.75 (broad s, 1H), 6.85-6.94 (m, 3H), 7.06-7.08 (m, 2H), 7.14-7.16 (m, 2H), 7.22-7.26 (m, 1H), 7.31-7.33 (m, 1H), 7.55-7.57 (m, 1H), 8.19-8.21 (m, 1H).

MS [(+)ESI, m/z]: 398 [M+H]$^+$.

Anal. Calcd. for $C_{26}H_{27}N_3O$: C 78.56, H 6.85, N 10.57. Found: C 78.75, H 6.96, N 10.60.

EXAMPLE 4

(4-Cyclohexyl-phenyl)-(5,11-dihydro-11-ethyl-5H-pyrido[2,3-b][1,5]benzodiazepin-6-yl)-methanone Sodium hydride (60% suspension in oil, 0.070 g, 1.75 mmol) was washed twice with hexane, dried under nitrogen and resuspended in dry N,N-dimethylformamide (10 mL). Following addition of (4-cyclohexyl-phenyl)-(5,11-dihydro-pyrido[2,3-b][1,5]benzodiazepin-6-yl)-methanone of Example 2 (0.49 g, 1.28 mmol), ethyl iodide (0.12 mL, 1.50 mmol) was added. After stirring for one hour, the reaction was quenched with water and extracted with dichloromethane. The organic layers were combined and dried over anhydrous sodium sulfate, filtered and concentrated in vacuo to give a yellow oil. Purification by flash chromatography using a solvent system of 30% ethyl acetate in hexane gave a colorless oil which crystallized by sonication from ethyl acetate/hexane to provide the title compound as a white solid (0.16 g, 30.4%), m.p. 130-132° C.

NMR (DMSO-$d_6$, 400 MHz): δ 1.11-1.35 (m, 8H), 1.63-1.73 (m, 5H), 2.40-2.44 (m, 1H), 3.90 (broad s, 1H), 4.20-4.50 (broad m, 2H), 5.73 (broad s, 1H), 6.84-6.87 (m, 1H), 6.93-6.95 (m, 2H), 7.03-7.09 (m, 2H), 7.20-7.25 (m, 3H), 7.35-7.37 (m, 1H), 7.54-7.55 (m, 1H), 8.17-8.19 (m, 1H).

MS [(+)ESI, m/z]: 412 [M+H]$^+$.

Anal. Calcd. for $C_{27}H_{29}N_3O$: C 78.80, H 7.10, N 10.21. Found: C 78.48, H 7.11, N 10.07.

EXAMPLE 5

(4-Cyclohexyl-phenyl)-(5,11-dihydro-10H-dibenzo[b,e][1,4]diazepin-10-yl)methanone To a suspension of 4-cyclohexylbenzoic acid (10.0 g) in dichloromethane (75 mL) was added oxalyl chloride (10.0 g) followed by N,N-dimethylformamide (2 drops). The mixture was stirred at room temperature overnight and then all volatiles were removed in vacuo to provide the crude acid chloride (11.0 g). 5,11-Dihydro-10H-dibenzo[b,e][1,4]diazepine (1.96 g) in dichloromethane (50 mL) containing N,N-diisopropylethyl amine (1.3 g) was reacted with the crude 4-cyclohexylbenzoyl chloride prepared as described above (2.22 g). The reaction mixture was kept at room temperature overnight, then washed with water and saturated aqueous sodium bicarbonate. The solution was dried over anhydrous sodium sulfate and filtered through a short column of Magnesol® which was eluted with several additional volumes of dichloromethane. The total effluent was refluxed with the gradual addition of hexane until crystallization was noted. Cooling and filtration afforded the title compound as colorless crystals (1.28 g), m.p. 175-176° C.

MS. [(+)ESI, m/z]: 383 [M+H]$^+$.

Anal. Calcd. for $C_{26}H_{26}N_2O$: C 81.64, H 6.85, N 7.32. Found: C 81.62, H 7.07, N 7.46.

EXAMPLE 6

(4-Cyclohexyl-phenyl)-(5,11-dihydro-5-methyl-10H-dibenzo[b,e][1,4]diazepin-10-yl)-methanone Step A. 1-(10,11-Dihydro-5H-dibenzo[b,e][1,4]diazepin-10-yl)-2,2,2-trifluoroethanone 10,11-Dihydro-5H-dibenzo[b,e][1,4]diazepine (3.88 g) in dichloromethane (100 mL) and N,N-diisopropylethyl amine (2.79 g) were cooled in an ice bath and trifluoroacetic anhydride (4.50 g) was slowly added. The reaction mixture was allowed to come to room temperature and stirring was continued overnight. The mixture was filtered and the filtrate washed with water and saturated aqueous sodium bicarbonate, and dried over anhydrous sodium sulfate. The organic extract was filtered through a short column of Magnesol® which was eluted with several additional volumes of dichloromethane. The total effluent was refluxed with the gradual addition of hexane until crystallization was noted. Cooling and filtration afforded the mono acylated title compound (3.34 g), m.p. 140-141° C.

Anal. Calcd. for $C_{15}H_{11}F_3N_2O$: C 61.65, H 3.79, N 9.58. Found: C 61.41, H 3.54, N 9.50.

Step B. 1-(10,11-Dihydro-5-methyl-dibenzo[b,e][1,4]diazepin-10-yl)-2,2,2-trifluoroethanone 1-(10,11-Dihydro-5H-dibenzo[b,e][1,4]diazepin-10-yl)-2,2,2-trifluoroethanone of Step A (3.12 g) was added to dry N,N-dimethylformamide (50 mL) containing sodium hydride (60% dispersion in oil, 0.60 g, washed with hexane). After a short while iodomethane was added (2.0 g) and the mixture stirred overnight at room temperature, quenched with ice and diluted with brine. The precipitate was collected and redissolved in dichloromethane. The solution was dried over anhydrous sodium sulfate and filtered through a short column of Magnesol® which was eluted with several additional volumes of dichloromethane. The total effluent was evaporated to dryness and the residue crystallized from hexane to provide the title compound as colorless crystals (1.23 g), m.p. 104-106° C.

MS [(+)ESI, m/z]: 307 [M+H]$^+$.

Anal. Calcd. for $C_{16}H_{13}F_3N_2O$: C 62.74, H 4.24, N 9.15, F 18.61. Found: C 62.73, H 4.20, N 9.11, F 18.26.

Step C. 10,11-Dihydro-5-methyl-dibenzo[b,e][1,4]diazepine 1-(10,11-Dihydro-5-methyl-dibenzo[b,e][1,4]diazepin-10-yl)-2,2,2-trifluoroethanone of Step B (1.0 g) in ethanol (25 mL) was treated with 1 N sodium hydroxide (10 mL). The reaction mixture was refluxed for five hours, cooled, all volatiles removed in vacuo and the residue triturated with water. The resulting solid was filtered off, redissolved in dichloromethane and dried over anhydrous sodium sulfate. The solution was filtered through a short column of Magnesol® which was eluted with several additional volumes of dichloromethane. The total effluent was evaporated to dryness to provide the title compound as an off-white crystalline solid (0.65 g), m.p. 115-117° C.

MS [(+)ESI, m/z]: 211 [M+H]$^+$.

Anal. Calcd. for $C_{14}H_{14}N_2$: C 79.97, H 6.71, N 13.32. Found: C 80.05, H 6.47, N 12.93.

Step D. (4-Cyclohexyl-phenyl)-(5,11-dihydro-5-methyl-10H-dibenzo[b,e][1,4]diazepin-10-yl-methanone A solution of 10,11-dihydro-5-methyl-dibenzo[b,e][1,4]diazepine of Step C (0.42 g) in dichloromethane (10 mL) containing N,N-diisopropylethyl amine (0.29 g) was treated with 4-cyclohexylbenzoyl chloride (0.50 g). After stirring overnight at room temperature, the reaction mixture was washed with water and saturated aqueous sodium bicarbonate, then dried over anhydrous sodium sulfate. The solution was filtered through a short column of Magnesol® which was eluted with several additional volumes of dichloromethane. Evaporation of all volatiles gave a glassy residue which was triturated with anhydrous diethyl ether to provide the title compound as an off-white crystalline solid (0.66 g), m.p. 111-112° C.

MS [(+)ESI, m/z]: 397 [M+H]$^+$.

Anal. Calcd. for $C_{27}H_{28}N_2O$: C 81.78, H 7.12, N 7.06. Found: C 81.53, H 7.36, N 6.93.

EXAMPLE 7

(4-Cyclohexyl-phenyl)-(4H,10H-3a,5,9-triaza-benzo[f]azulen-9-yl)-methanone

Step A. 2-Chloromethyl-pyridine-3-carboxylic acid methyl ester

A solution of methyl 2-methylnicotinate (20.0 g, 0.132 mol) and trichloroisocyanuric acid (46.0 g, 0.198 mol) in dichloromethane (100 mL) was stirred at room temperature overnight. The reaction mixture was then washed with saturated aqueous sodium carbonate and saturated aqueous sodium chloride, dried over anhydrous magnesium sulfate, filtered, and the solvent evaporated in vacuo to provide the title compound as a yellow liquid (11.2 g), which was used as such in the next step.

Step B. 2-(2-Formyl-pyrrol-1-yl-methyl)-pyridine-3-carboxylic acid methyl ester

To a suspension of sodium hydride (5.8 g, 0.12 mol), in dry N,N-dimethyl formamide (25 mL) was added slowly under nitrogen a solution of pyrrole 2-carboxaldehyde (10.5 g, 0.11 mol) in N,N-dimethylformamide (10 mL), and the reaction mixture was stirred at room temperature for 30 minutes. The reaction was then cooled to 5° C. and 2-chloromethyl-pyridine-3-carboxylic acid methyl ester of Step A was added slowly, the temperature being maintained at or below 20° C. After the addition was complete, the reaction was stirred at room temperature for 30 minutes. The mixture was evaporated to dryness, and the residue was dissolved in ethyl acetate (250 mL). This solution was washed with water and dried over anhydrous magnesium sulfate. The solvent was then removed in vacuo leaving a dark crystalline solid (23.4 g), which was purified by chromatography on silica gel eluting with a gradient of ethyl acetate/petroleum ether to provide the title compound as a tan crystalline solid (13.75 g), m.p. 91-93° C.

Step C. [3-(2-Formyl-pyrrol-1-yl-methyl)-pyridin-2-yl]-carbamic acid benzyl ester To a stirred solution of 2-(2-formyl-pyrrol-1-yl-methyl)-pyridine-3-carboxylic acid methyl ester of Step B (13.65 g, 55.9 mmol) in methanol (50 mL) was added sodium hydroxide (2.2 g, 55.9 mmol). The reaction mixture was refluxed under nitrogen for 2 hours, and then the solvent was removed in vacuo. A portion of the residual yellow solid. (5 g) was suspended in a mixture of benzyl alcohol (20 mL) and benzene (30 mL). Diphenylphosphoryl azide (6.54 g, 1.2 equiv.) was added, and the reaction was slowly heated to reflux. After refluxing for 1 hour, the mixture was cooled and washed with water, dried over anhydrous magnesium sulfate, filtered and evaporated to dryness to provide the title compound as a tan crystalline solid (4.4 g), m.p. 109-111° C.

Step D. 9,10-Dihydro-4H-3a,5,9-triaza-benzo[f]azulene

A stirred mixture of [3-(2-formyl-pyrrol-1-yl-methyl)-pyridin-2-yl]carbamic acid benzyl ester of Step C (1.0 g), in ethyl acetate (10 mL) containing 10% palladium on charcoal (10 mg), magnesium sulfate (0.010 g) and 5 drops of acetic acid was hydrogenated at atmospheric pressure until hydrogen uptake ceased. The reaction mixture was then filtered through Celite and the solvent removed in vacuo. The crude product (yellow crystalline solid, 0.530 g) was purified by chromatography on silica gel eluting with a gradient of ethyl acetate in petroleum ether to provide the title product as a yellow crystalline solid, m.p. 171-172° C.

Step E. (4-Cyclohexyl-phenyl)-(4H,10H-3a,5,9-triaza-benzo[f]azulen-9-yl)-methanone A mixture of the 9,10-dihydro-4H-3a,5,9-triaza-benzo[f] azulene of Step D (4.67 mmol), 4-cyclohexylbenzoyl chloride (4.90 mmol) and triethylamine (5.1 mmol) in 1,2-dichloroethane was refluxed for three days under nitrogen. The solvent was removed in vacuo and the residue chromatographed on silica gel eluting with a solvent gradient from 5 to 20% of ethyl acetate in hexane to provide the title compound as a tan solid (0.684 g), m.p. 150-152° C.

NMR (400 MHz, DMSO-$d_6$): δ 1.2-1.4 (m, 6H), 1.6-1.8 (m, 5H), 5.05 (s, 2H), 5.4 (s, 2H), 5.9 (m, 1H), 6.0 (s, 1H), 6.9 (m, 1H), 7.1 (m, 3H), 7.2 (m, 3H), 7.3 (d, 1H).

MS [(+)APCI, m/z]: 372 [M+H]$^+$.

Anal. Calcd. for $C_{24}H_{25}N_3O$: C 77.60, H 6.78, N 11.31. Found: C 76.65, H 6.83, N 11.16.

EXAMPLE 8

(4-Cyclohexyl-phenyl)-(5,6,7,8-tetrahydro-thieno[3,2-b]azepin-4-yl)-methanone

A solution of 4-cyclohexyl-benzoic acid (0.479 g) in tetrahydrofuran (10 ml) was treated with N,N-dimethylformamide (20 µl) followed by dropwise addition of oxalyl chloride (0.260 ml). When the gas evolution stopped the solution was warmed to reflux for 5 minutes, then cooled and concentrated in vacuo to an oil. The oil was diluted with tetrahydrofuran (5 ml) and again concentrated in vacuo. This cycle was repeated one more time and then the oil was dissolved in dichloromethane (15 ml). A solution of 5,6,7,8-tetrahydro-4H-thieno[3,2-b]azepine (0.300 g) and Hunig's base (1.1 equiv.) in dichloromethane (25 ml) was cooled to 0° and treated dropwise with the previously prepared solution of 4-cyclohexylbenzoyl chloride. The reaction was stirred overnight as the temperature was allowed to return to room temperature. The solution was washed sequentially with 0.1N hydrochloric acid, 50% saturated aqueous sodium bicarbonate solution and brine. The organic layer was dried over anhydrous sodium sulfate, filtered and evaporated in vacuo. The residual oil was flash chromatographed on silica gel using 15% ethyl acetate in hexanes as the eluant to provide the title compound (0.54 g) as an orange tinged solid.

m.p. 145-148° C.

IR (KBr, cm$^{-1}$): 1630

MS [(+)APCI, m/z]: 340 [M+H]$^+$.

NMR (400 MHz, CDCl$_3$): δ 1.22 (t, 1H), 1.34 (m, 4H), 1.79 (m, 7H), 2.0 (br s, 2H), 2.43 (br s, 1H), 3.86 (dd, 2H), 4.01 (br s, 2H), 6.18 (br s, 1H), 6.62 (br s, 1H), 7.04 (d, 2H), 7.20 (m, 2H).

Anal Calcd for $C_{21}H_{25}NOS$: C, 74.29; H 7.42; N 4.13. Found: C 74.09; H 7.50; N 4.02.

What is claimed is:

1. A compound of the formula (I):

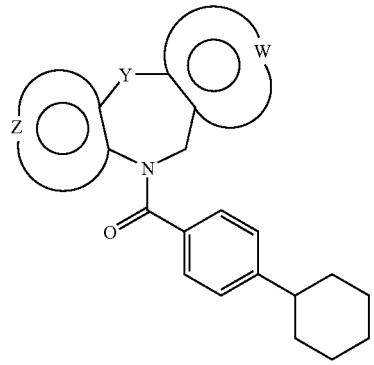

wherein:
Y is —(CH$_2$)$_n$—,
wherein n is 1;

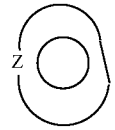

represents (1) a phenyl ring optionally substituted with one or two substituents selected, independently, from the group consisting of hydrogen, ($C_1$-$C_6$) lower alkyl, halogen, cyano, $CF_3$, hydroxy, ($C_1$-$C_6$) lower alkoxy, ($C_1$-$C_6$) lower alkoxy carbonyl, carboxy, —CONH$_2$, —CONH[($C_1$-$C_6$) lower alkyl], and —CON[($C_1$-$C_6$) lower alkyl]$_2$; or (2) a 6-membered aromatic (unsaturated) heterocyclic ring having one nitrogen atom, optionally substituted by ($C_1$-$C_6$) lower alkyl, halogen or ($C_1$-$C_6$) lower alkoxy;

represents (1) a phenyl ring optionally substituted with one or two substituents selected, independently, from the group consisting of hydrogen, ($C_1$-$C_6$) lower alkyl, halogen, cyano, $CF_3$, hydroxy, ($C_1$-$C_6$) lower alkoxy, ($C_1$-$C_6$) lower alkoxy carbonyl, carboxy, —CONH$_2$, —CONH[($C_1$-$C_6$) lower alkyl], and —CON[($C_1$-$C_6$) lower alkyl]$_2$; (2) a 5-membered aromatic (unsaturated) heterocyclic ring having one nitrogen atom, optionally substituted by ($C_1$-$C_6$) lower alkyl, ($C_1$-$C_6$) lower alkoxy, or halogen; or (3) a 6-membered aromatic (unsaturated) heterocyclic ring having one nitrogen atom, optionally substituted by ($C_1$-$C_6$) lower alkyl, halogen, or ($C_1$-$C_6$) lower alkoxy;

or a pharmaceutically acceptable salt thereof.

2. A compound according to claim 1 which is (4-cyclohexyl-phenyl)-(4H, 10H-3a,5,9-triaza-benzo[f]azulen-9-yl)-methanone or a pharmaceutically acceptable salt thereof.

3. A method of treating diabetes insipidus, nocturnal enuresis, nocturia, urinary incontinence, or bleeding and coagulation disorders in a mammal, the method comprising administering to the mammal in need thereof a pharmaceutically effective amount of a compound of claim 1, or a pharmaceutically acceptable salt thereof.

4. A method of inducing temporary delay of urination in a mammal, the method comprising administering to a mammal in need thereof a pharmaceutically effective amount of a compound of claim 1, or a pharmaceutically acceptable salt thereof.

5. A pharmaceutical composition comprising a pharmaceutically effective amount of a compound of claim 1 and a pharmaceutically acceptable carrier.

6. A compound according to claim 1 having the formula (Ia):

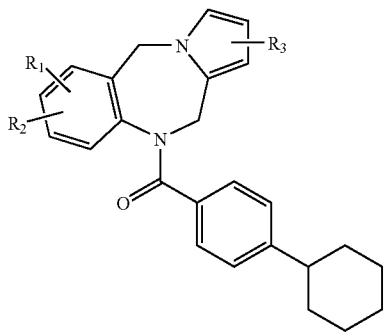

(Ia)

wherein:
$R_1$ and $R_2$ are independently selected from H, $(C_1-C_6)$ lower alkyl, halogen, CN, $CF_3$, OH, $(C_1-C_6)$ lower alkoxy carbonyl, carboxy, —$CONH_2$, $CONH[(C_1-C_6)$ lower alkyl], and —$CON[(C_1-C_6)$ lower alkyl]$_2$; and $R_3$ is selected from the group of $(C_1-C_6)$ lower alkyl, $(C_1-C_6)$ lower alkoxy, and halogen; or a pharmaceutically acceptable salt thereof.

7. A compound according to claim 1 having the formula (Id):

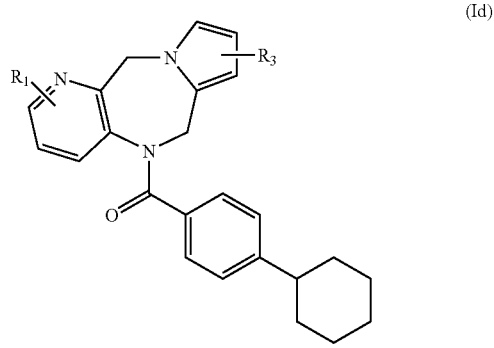

(Id)

wherein:
$R_1$ is selected from $(C_1-C_6)$ lower alkyl, halogen, and $(C_1-C_6)$ lower alkoxy; and $R_3$ is selected from the group of $(C_1-C_6)$ lower alkyl, $(C_1-C_6)$ lower alkoxy, and halogen; or a pharmaceutically acceptable salt thereof.

8. A compound according to claim 1, which is 10-(4-cyclohexyl-benzoyl)-10,11-dihydro-5H-pyrrolo[2,1-c][1,4]benzodiazepine, or pharmaceutically acceptable salt thereof.

* * * * *